US00PP17702P3

(12) United States Plant Patent
Sanders

(10) Patent No.: US PP17,702 P3
(45) Date of Patent: May 8, 2007

(54) **MINI *IMPATIENS* PLANT NAMED 'IMMIVOIL'**

(50) Latin Name: *Impatiens walleriana*
Varietal Denomination: Immivoil

(75) Inventor: Monica Maria Adelheid Sanders, Grootebroek (NL)

(73) Assignee: Syngenta Seeds B.V., Enkhuizen (NL)

( * ) Notice: Subject to any disclaimer, the term of this patent is extended or adjusted under 35 U.S.C. 154(b) by 144 days.

(21) Appl. No.: 11/221,958

(22) Filed: Sep. 8, 2005

(65) Prior Publication Data

US 2007/0056068 P1 Mar. 8, 2007

(51) Int. Cl.
*A01H 5/00* (2006.01)

(52) U.S. Cl. ..... Plt./317

(58) Field of Classification Search ..... Plt./317
See application file for complete search history.

*Primary Examiner*—Kent Bell
*Assistant Examiner*—Annette H Para
(74) *Attorney, Agent, or Firm*—Bruce Vrana

(57) ABSTRACT

A new and distinct cultivar of mini *Impatiens* plant characterized by its small red purple flowers, freely flowering habit, dark green foliage, and bushy shaped growth habit with excellent basal branching.

1 Drawing Sheet

Latin name of the genus and species of the plant claimed: *Impatiens wallerina.*
Varietal denomination: 'Immivoil'.

BACKGROUND OF THE NEW PLANT

The present invention comprises a new and distinct mini *Impatiens* plant botanically known as *Impatiens walleriana* and referred to by the cultivar name 'Immivoil'.

The new cultivar was developed in a controlled breeding program in Enkhuizen, Netherlands. The new mini *Impatiens* cultivar is characterized by small red purple flowers, freely flowering habit, dark green foliage, and bushy shaped growth habit with excellent basal branching.

The new cultivar is propagated from cuttings resulting from the cross in March 1999 of the proprietary mini *Impatiens* selection identified as 'Q138-4' as female parent and the proprietary mini *Impatiens* selection identified as 'Q138-3' as male parent. 'Q138-4' is not commercially available and has not been patented. 'Q138-3' is not commercially available and has not been patented.

The present cultivar was selected in August 1999 in Enkhuizen, Netherlands and has been repeatedly asexually reproduced by cuttings over a period of several years. The distinctive characteristics of this new mini *Impatiens* are stable and reproduced true to type in successive generations of asexual reproduction. It takes 6 to 8 weeks to produce a finished plant, starting from a rooted plug and planted in a 10 cm pot, depending on the temperature.

SUMMARY OF THE INVENTION

The following traits have been repeatedly observed and are determined to be the unique characteristics of 'Immiviol.' These characteristics in combination distinguish 'Immiviol' as a new and distinct mini *Impatiens* cultivar:

1. Small red purple flowers.
2. Bushy shaped growth habit with many flowers on top of the foilage.

3. Dark green foliage.
4. Excellent basal branching.

Plants of the new mini *Impatiens* differ primarily from the plants of the female parent selection in the following characteristics:

Plants of the new mini *Impatiens* have small red purple flowers, whereas the plants of the female have large red purple flowers.

Plants of the new mini *Impatiens* differ primarily from the plants of the male parent selection in the following characteristics:

Plants of the mini *Impatiens* hve small red purple flowers, whereas the plants of the male have large red purple flowers.

Plants of the new mini *Impatiens* can be compared to plants of 'Fify violet' disclosed in U.S. Plant Pat. No. 11,557. In side-by-side comparisons conducted by the inventor in Enkhuizen, Netherlands, the plants of the new mini *Impatiens* differed from plants of the cultivar 'Fify violet' in the following characteristics:

1. Plants of the new mini *Impatiens* have dark green leaves, whereas plants of the cultivar 'Fify violet' have green leaves.
2. Plants of the new mini *Impatiens* have red purple flowers, whereas the cultivar 'Fify violet' had medium red purple flowers.

DESCRIPTION OF THE DRAWING

This new mini *Impatiens* plant is illustrated by the accompanying photographic drawing which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new mini *Impatiens*. The data which defines these characteristics were collected from asexual reproductions carried out in Enkhuizen, Netherlands. The plant history was taken on 20 week old plants, blossomed under natural light in the field.

Color readings were taken in the laboratory under ambient light. Color references are primarily to The R.H.S. Colour Chart of The Royal Horticultural Society of London.

The plant:
*Classification.*—Botanical: *Impatiens walleriana.*
*Parentage:*
*Female parent.*—Proprietary *Impatiens walleriana* selection identified as code number 'Q138-4,' not patented.
*Male parent.*—Proprietary *Impatiens walleriana* selection identified as code number 'Q138-3,' not patented.
Propagation:
*Type cutting.*—Terminal cuttings.
*Time to initiate roots.*—About 10–21 days at 22–23 degrees C.
*Time to produce a rooted cutting.*—About 28 days at 16–24 degrees C.
*Root description.*—Fine, fibrous, and white in color.
Plant description:
*General appearance.*—Compact, upright, outwardly spreading and mounded plant habit.
*Growth and branching habit.*—Moderately vigorous and freely branching growth habit lateral branches potentially forming at every node, dense and bushy shaped growth habit. Pinching enhances branching.
*Plant height.*—About 10 cm.
*Plant diameter or spread.*—About 23 cm.
Lateral branch description:
*Length.*—About 7 cm.
*Diameter.*—About 5 mm.
*Internode length.*—About 5–20 mm.
*Texture.*—Smooth, glabrous.
*Color.*—RHS 147B Yellow-green with a few stripes anthocyanic RHS 64A Red-purple.
Foliage description:
*Arrangement: Alternate, simple.*
*Length.*—About 2 cm.
*Width.*—About 2.3 cm.
*Shape.*—Ovate.
*Apex.*—Acuminate.
*Base.*—Attenuate.
*Margin.*—Slightly crenate with minute ciliation.
*Texture, upper and lower surfaces.*—Smooth, glabrous.
*Venation pattern.*—Pinnate.
*Color.*—Developing and fully expanded foliage, Upper surface: RHS 137A Green. Developing and fully expanded foliage, Lower surface: RHS 137C Green. Venation, upper and lower surfaces: RHS 147B Yellow-green.
Petiole:
*Length.*—About 1.5 cm.
*Diameter.*—About 2 mm.
*Texture, upper and lower surfaces.*—Smooth, glabrous.
*Color.*—RHS 147C Yellow-green.
Flower description:
*Flower type and habit.*—Numerous small single flowers.
*Flowers arise from leaf axils.*—Freely flowering, usually about 40 flowers and flower buds per lateral branch.
*Flower position.*—Above the foliage and typically face upright or outward.
*Flowers lasting.*—About 5–7 days on the plant under greenhouse conditions.
*Flowers.*—Persistent and not fragrant.
*Flowering season.*—Continuous through the spring and summer.
Flower size:
*Height.*—About 2 cm.
*Diameter.*—About 1.5–2.0 cm.
*Depth.*—About 5 mm.
Flower buds:
*Length.*—About 7 mm.
*Diameter.*—About 4 mm.
*Shape.*—Ovoid.
*Color.*—RHS 146D Yellow-green with RHS 64B Red-purple.
Petals:
*Quantity/arrangement.*—Five per flower in a single whorl.
*Length, banner petal.*—About 1 cm.
*Length, lateral petals.*—About 1 cm.
*Length, basal petals.*—About 1.2 cm.
*Width, banner petal.*—About 1.3 cm.
*Width, lateral petals.*—About 7 mm.
*Width, basal petals.*—About 9 mm.
*Shape.*—Obovate to ovate.
*Apex.*—Rounded or slightly emarginate.
*Base.*—Attenuate.
*Margin.*—Entire.
*Texture, upper and lower surfaces.*—Smooth, glabrous.
*Color.*—When opening, upper surface: RHS 61A Red-purple. When opening, lower surface: RHS 71B Red-purple. Fully opened, banner petal, upper surface: RHS 61A Red-purple. Fully opened, lateral petals, upper surface: RHS 61A Red-purple. Fully opened, basal petals, upper surface: RHS 61A Red-purple. Fully opened, lower surface: RHS 71B Red-purple.
Sepals:
*Quantity/arrangement.*—Five in a single whorl, one modified into an elongated spur.
*Calyx length.*—About 3 mm.
*Calyx diameter.*—About 1 mm.
*Shape.*—Ovate.
*Apex.*—Acute.
*Margin.*—Entire.
*Texture, upper and lower surfaces.*—Smooth, glabrous.
*Color, upper and lower surfaces.*—RHS 147C Yellow-green.
*Spur length.*—About 2 cm.
*Spur diameter.*—At flower, about 2 mm, at apex, less than 1 mm.
*Spur color.*—RHS 58D Red-purple at flower, at apex RHS 64A Red-purple.
Peduncles:
*Length.*—About 1 cm.
*Diameter.*—About 1 mm.
*Angle.*—About 45° from vertical.
*Strength.*—Strong.
*Texture.*—Smooth, glabrous.
*Color.*—RHS 148B Yellow-green.
Reproductive organs:
Stamens:
*Quantity.*—Five fused around stigma.
*Anther length.*—About 2 mm.

*Anther color.*—RHS 61A Red-purple.
*Pollen amount.*—None observed.
*Pistils.— Quantity per flower.*—One.
*Pistil length.*—About 3 mm.
*Stigma shape.*—Rounded.
*Stigma color.*—RHS 61A Red-purple.
*Style color.*—RHS 147A Yellow-green.
*Ovary color.*—RHS 147A Yellow-green.
*Seed/fruit.*—Seed and fruit production has not been observed.

Disease and pest resistance: Plants of the new *Impatiens* have not been observed to be resistant to pathogens and pests common to *Impatiens*.

What is claimed is:

1. A new and distinct cultivar of mini *Impatiens* plant named 'Immiviol', as substantially illustrated and described herein.

* * * * *

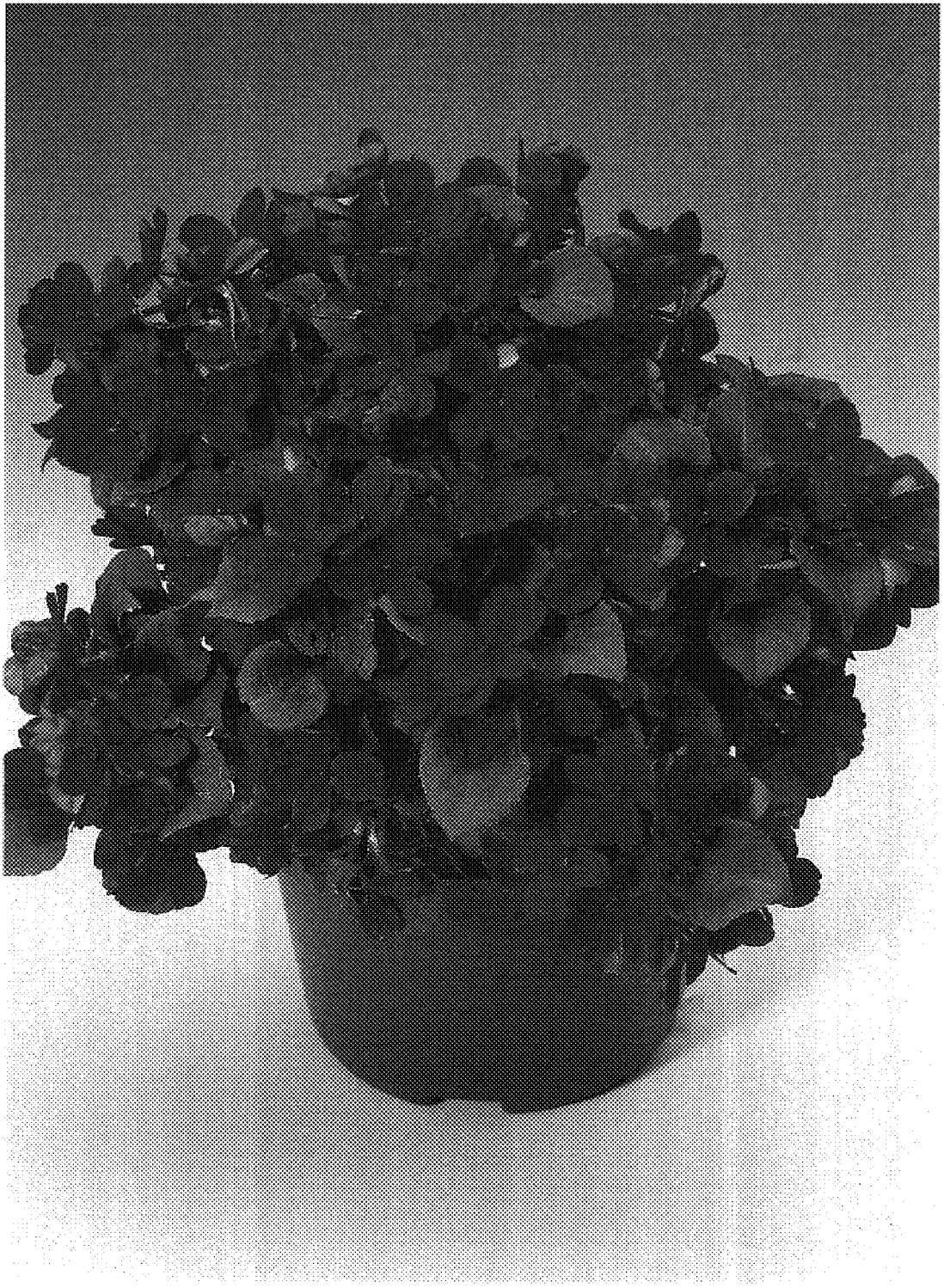

UNITED STATES PATENT AND TRADEMARK OFFICE

CERTIFICATE OF CORRECTION

PATENT NO. : PP 17,702 P3
APPLICATION NO. : 11/221958
DATED : May 8, 2007
INVENTOR(S) : Sanders It is certified that error appears in the above-identified patent and that said Letters Patent is hereby corrected as shown below:

Title Page, Column 1, item (54), Title, delete "'IMMIVOIL'" and insert therefor --'IMMIVIOL'--

Title Page, Column 1, item (50), Varietal Denomination, delete "Immivoil" and insert therefor --Immiviol--

Title Page, Column 1, line 3, Varietal denomination, delete "'Immivoil'" and insert therefor --'Immiviol'--

Title Page, Column 1, line 9, delete "'Immivoil'" and insert therefor --'Immiviol'--

Signed and Sealed this

Twenty-first Day of August, 2007

JON W. DUDAS
*Director of the United States Patent and Trademark Office*